US006846496B1

(12) United States Patent
Timonen et al.

(10) Patent No.: US 6,846,496 B1
(45) Date of Patent: Jan. 25, 2005

(54) TREATMENT OF OSTEOPOROSIS

(75) Inventors: Ulla Timonen, Kirkkonummi (FI); Raija Vaheri, Helsinki (FI)

(73) Assignee: Orion Corporation, Espoo (FI)

( * ) Notice: Subject to any disclaimer, the term of this patent is extended or adjusted under 35 U.S.C. 154(b) by 185 days.

(21) Appl. No.: 10/110,544

(22) PCT Filed: Oct. 13, 2000

(86) PCT No.: PCT/FI00/00890

§ 371 (c)(1),
(2), (4) Date: Apr. 15, 2002

(87) PCT Pub. No.: WO01/26640

PCT Pub. Date: Apr. 19, 2001

Related U.S. Application Data

(60) Provisional application No. 60/159,501, filed on Oct. 15, 1999.

(51) Int. Cl.[7] .................................................. A61K 9/20
(52) U.S. Cl. ...................................................... 424/464
(58) Field of Search ................................. 424/464, 451

(56) References Cited

U.S. PATENT DOCUMENTS

| | | | |
|---|---|---|---|
| 5,541,172 | A | 7/1996 | Labrie et al. |
| 5,567,695 | A | 10/1996 | Labrie |
| 5,622,973 | A | 4/1997 | Morriello et al. |
| 5,646,116 | A | 7/1997 | Bürk |
| 5,776,923 | A | 7/1998 | Labrie |
| 5,804,590 | A | 9/1998 | Fujiwara et al. |
| 5,858,394 | A | 1/1999 | Lipp et al. |
| 5,898,038 | A | 4/1999 | Yallampalli et al. |
| 5,900,255 | A | 5/1999 | Ohta et al. |
| 5,904,931 | A | 5/1999 | Lipp et al. |

FOREIGN PATENT DOCUMENTS

| | | |
|---|---|---|
| EP | 0393539 | 10/1990 |
| EP | 0461290 | 12/1991 |
| WO | 9522332 | 8/1995 |

OTHER PUBLICATIONS

E.F. Eriksen et al., "European and North American Experience with HRT for the Prevention of Osteoporosis," Bone, vol. 19, No. 5, Supplement, Nov. 1996:179S–183S.

"European consensus development conference on menopause," Human Reproduction, vol. 11, No. 5, pp. 975–979, 1996.

"Physicans Desk Reference," PDR 58 Edition, 2004, pp. 3464–3471.

"Electronic Medicines Compendium," description of INDIVINA at www.emec.medicines.org.uk, last updated on Jun. 11, 2003.

Heikkinen J E et al.; "Optimizing continuous–combined hormone replacement therapy for postmenopausal women: a comparison of six different treatment regimens"; AM J Obstest Gynecol. vol. 182; No. 3; Mar. 2000; pp. 560–567.

Heikkinen J et al.; "Low–dose continous HRT increases BMD in postmenopausal women"; Maturitas; vol. 35; No. 1; Jun. 2000; pp. s66–s67.

Heikkinen J et al.; "Effects of long–term continuous combined HRT on endometrial histology"; Maturitas; vol. 35; Jun. 2000; p. s67.

Timonen U et al.; "Comparison of three continous combined estrogen–progestin regimens"; Maturitas; vol.35; No. 1; Jun. 2000; p. s67.

*Primary Examiner*—James M. Spear
(74) *Attorney, Agent, or Firm*—Finnegan, Henderson, Farabow, Garrett & Dunner, LLP

(57) ABSTRACT

A method for the prevention or treatment of postmenopausal osteoporosis by initiating the treatment with a low close of an estrogenic compound and increasing the dose of the estrogenic compound after the initiation period.

12 Claims, 2 Drawing Sheets

Change (%)

0 2 4 6 8 10

6 months 12 months 24 months 36 months 48 months

A B C

Treatment A: 1 mg $E_2V$ + 2.5 or 5 mg MPA for 6 months, then E2V dose increased to 2 mg.
Treatment B: 2 mg $E_2V$ + 2.5 or 5 mg MPA
Treatment C: 1 mg $E_2V$ + 2.5 or 5 mg MPA Treatment A: 1 mg $E_2V$ + 2.5 or 5 mg MPA for 6 months, then E2V dose increased to 2 mg.
Treatment B: 2 mg $E_2V$ + 2.5 or 5 mg MPA
Treatment C: 1 mg $E_2V$ + 2.5 or 5 mg MPA Treatment A: 1 mg $E_2V$ + 2.5 or 5 mg MPA for 6 months, then E2V dose increased to 2 mg.
Treatment B: 2 mg $E_2V$ + 2.5 or 5 mg MPA
Treatment C: 1 mg $E_2V$ + 2.5 or 5 mg MPA

TREATMENT OF OSTEOPOROSIS

This application is a national stage filing of PCT International Application No. PCT/FI00/00890, filed on Oct. 13, 2000. This application also claims the benefit of priority to U.S. provisional patent application No. 60/159,501, filed on Oct. 15, 1999.

FIELD OF THE INVENTION

The present invention relates in general to a method for the prevention or treatment of postmenopausal osteoporosis. Accordingly, the present invention relates to a new method for the prevention or treatment of postmenopausal osteoporosis which comprises initiating the treatment with a low dose of an estrogenic compound and after the initiation period increasing the dose of the estrogenic compound. The present invention also relates to the use of an estrogenic compound in the manufacture of a medicament for the prevention or treatment of postmenopausal osteoporosis characterized in that the treatment is initiated with a low dose of an estrogenic compound and after the initiation period the dose of the estrogenic compound is increased.

BACKGROUND OF THE INVENTION

Osteoporosis is a systemic skeletal disease characterized by low bone mass and microarchitectural deterioration of bone tissue, with a consequent increase in bone fragility and susceptibility to fracture. It is a significant cause of mortality and morbidity in the elderly people, both of individual and community perspective. Osteoporosis affects an estimated 75 million people in Europe, the United States and Japan.

The number of postmenopausal women has been increasing steadily with the ageing population. One of the most common types of osteoporosis is associated with menopause. Annual losses of 2–6% of bone mass have been reported to occur in women in early postmenopause.

Conventional estrogen preparations are currently used for the treatment of postmenopausal osteoporosis. One such preparation is a sequentially administered preparation containing 2 mg of estradiol valerate combined with 10 mg of medroxyprogesterone acetate (Divina®, Orion Corporation, Espoo, Finland).

SUMMARY OF THE INVENTION

The present invention provides a method for the prevention and treatment of postmenopausal osteoporosis. The method comprises initiating the treatment with a low dose of an estrogenic compound, and after the initiation period, increasing the dose of the estrogenic compound. Particularly, the present invention relates to a method for the prevention and treatment of postmenopausal osteoporosis which comprises initiating the treatment with a low dose of an estrogenic compound and after the initiation period doubling the dose of the estrogenic compound. The initiation period of the treatment usually lasts about 4 to 8 months, preferably 6 months.

In a further aspect, the invention relates to the use of an estrogenic compound in the manufacture of a medicament for the prevention or treatment of postmenopausal osteoporosis characterized in that the treatment is initiated with a low dose of an estrogenic compound and after the initiation period the dose of the estrogenic compound is increased.

DETAILED DESCRIPTION OF THE INVENTION

Figure 1:
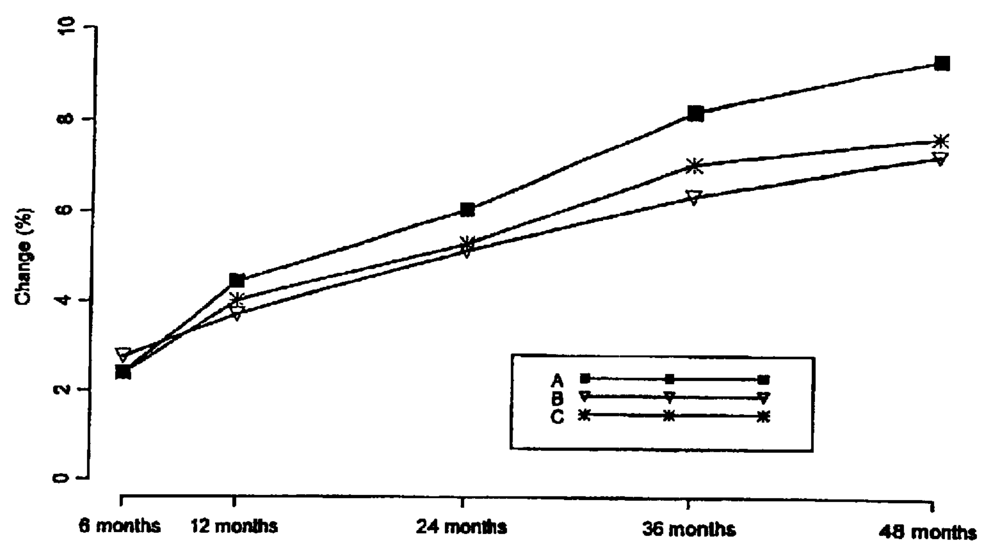
FIG. 1 shows the change (%) in bone mineral density in osteopenic and osteoprotic women in lumbar spine.

The inventors suprisingly discovered that when treating postmenopausal osteoporosis by initiating the treatment with a low dose of an estrogenic compound and increasing the dose of the estrogenic compound after this initiation period, the increase in bone mineral density was higher than when treating postmenopausal osteoporosis by administering the same dose of the estrogenic compound (either the low dose or the increased dose) for the whole term of the treatment. Particularly, it was found that in patients whose daily dose of the estrogenic compound was increased after the first 6 months of the treatment from 1 mg of estradiol valerate ($E_2V$) to 2 mg of $E_2V$, the increase in bone mineral density in the vertebrae, expressed as a percentage, was 8.9% after the treatment term of 48 months. Analogously, the increase in bone mineral density, expressed as a percentage, was 6.2% and 7.4% in patients whose daily estrogen dose during the whole treatment term was either 1 mg of $E_2V$ or 2 mg of $E_2V$ respectively. The corresponding values in the femoral neck were 4.2%, 2.9% and 2.9%. Further, it was found that in osteopenic and osteoporotic patients whose daily dose of the estrogenic compound was increased after the first 6 months of the treatment from 1 mg of $E_2V$ to 2 mg of $E_2V$, the increase in bone mineral density in the vertebrae, expressed as a percentage, was 9.4% after the treatment term of 48 months. Analogously, the increase in bone mineral density, expressed as a percentage, was 7.7% and 7.3% in patients whose daily estrogen dose during the whole treatment term was either 1 mg of E2V or 2 mg of $E_2V$, respectively. In osteopenic and osteoporotic patients the corresponding values in the femoral neck were 6.4%, 3.8% and 3.5%.

Accordingly, an object of the present invention is a method for the prevention or treatment of postmenopausal osteoporosis which comprises initiating the treatment with a low dose of an estrogenic compound and after this initiation period increasing the dose of the estrogenic compound. Particularly, the present invention relates to a method for the prevention and treatment of postmenopausal osteoporosis which comprises initiating the treatment with a low dose of an estrogenic compound and after this initiation period doubling the dose of the estrogenic compound. The initiation period of the treatment usually lasts about 4 to 8 months, preferably 6 months.

The low dose of an estrogenic compound used during the initiation period is a dose equivalent in estrogenic activity to approximately 0.5 mg–1.5 mg of estadiol valerate. Preferably, the low dose of an estrogenic compound is a dose equivalent in estrogenic activity to approximately 1 mg of estradiol valerate.

The increased dose of an estrogenic compound used during the rest of the treatment term is a dose equivalent in estrogenic activity to approximately 1 mg–3 mg of estradiol valerate. Preferably, the increased dose of an estrogenic compound is a dose equivalent in estrogenic activity to approximately 2 mg of estradiol valerate.

The estrogenic compound of the present invention is preferably estradiol valerate. Other conventional estrogens such as estrone, estrone sulfate, estrone sulphate piperazine salts and their esthers as well as synthetic estrogens may also be employed.

EXAMPLE

In order to demonstrate the effectiveness of using the method of the present invention, and its advantages, a comparative study was undertaken to evaluate the efficacy and tolarability of the method. The subjects used in the study were 419 postmenopausal women, aged 45 to 65 years. Eligible women had to be at least 3 years postmenopausal with normal gynecological findings, an intact uterus and a body mass index of 30 or less. Major medical exclusion criteria included endometrial hyperplasia and pathological mammography findings, prior hormone-dependent malignancies, severe thyroid diseases, and other criteria typical for HRT studies. Excessive smokers and alcohol abusers were excluded. Otherwise the women were not required to change their daily diet or other lifestyle habits for the study period. The women did not take any calcium or vitamin D supplementation during the study period.

Subjects were randomly assigned to six treatment groups to receive one tablet daily containing one of the following dose combinations: 1 mg or 2 mg of estradiolvalerate ($E_2V$) combined to 2.5 mg or 5 mg of medroxyprogestrone acetate (MPA) (Indivina®, Orion Corporation, Espoo, Finland).

| Group | Daily $E_2V$ dose (First 6 mo/After 6 mo) | Daily MPA dose |
|---|---|---|
| Group I | 1 mg/2 mg | 2.5 mg |
| Group II | 1 mg/2 mg | 5 mg |
| Group III | 2 mg/2 mg | 2.5 mg |
| Group IV | 2 mg/2 mg | 5 mg |
| Group V | 1 mg/1 mg | 2.5 mg |
| Group VI | 1 mg/1 mg | 5 mg |

Groups changing from 1 mg $E_2V$ to 2 mg $E_2V$ irrespective of the MPA (Group I and II) were pooled together. Groups receiving 1 mg of $E_2V$ throughout the study irrespective of the MPA dose (Group V and VI) were pooled together. Also groups receiving 2 mg of $E_2V$ throughout the study irrespective of the MPA dose (Group III and IV) were pooled together. Pooling was considered justified since MPA is not expected to affect the response of estrogen on bone mineral density (BMD).

The bone mineral densities at the vertebrae and the hip were measured using dual-energy X-ray absorptiometry (DPX) at baseline, 6-, 12-, 24, 36- and 48-month follow-up visits, and at premature discontinuation. The BMD from the hip was measured by three separate measurements at the femur neck, Ward's triangle, major trochanter and BMD from the vertebrae was measured at L2–L4. In addition, the area and bone mineral content (BMC) of vertebrae L2–L4 were determined.

Bone Mineral Density at 48 Months

Both vertebral and femoral bone mineral densities increased in all three groups. The increases were more pronounced at the vertebrae, but significant improvement was also observed at all indices at the hip (femoral neck, trochanter and Ward's triangle).

Pooled Results of All Subjects

In the vertebrae there was a statistically significant difference in favor of the 2 mg estrogen dose. The mean percentage change was 7.4% in the group receiving 2 mg of $E_2V$ compared to 6.2% in the group receiving 1 mg of $E_2V$ ($p=0.0079$). Similarly, BMD response in group switching from 1 mg to 2 mg $E_2V$ differed statistically significantly from 1 mg $E_2V$ group 8.9%, ($p<0.001$).

In the femoral neck no significant difference could be seen between lower and higher estrogen dose groups, but the group switching from 1 mg to 2 mg had statistically significantly larger BMD response compared to 1 mg of $E_2V$ group (4.3% vs. 2.9%, $p=0.0361$).

Osteopenic/osteoporotic vs Normal Bones in Pooled Groups

Results were further analysed to compare the effect varying dosages on BMD in groups that had either normal, osteopenic or osteoporotic BMD value at baseline. Subjects were classified as osteopenic if the BMD was 0.90 to 1.08 g/cm$^2$ in vertebrae (L2–L4) and 0.68 to 0.86 g/cm$^2$ in femoral neck (corresponds to T score between −1 and −2.5 in Finnish population). BMD was regarded as normal if the values were above 1.08 g/cm$^2$ in vertebrae and above 0.86 g/cm$^2$ in femoral neck. Values below 0.90 g/cm$^2$ in vertebrae and below 0.68 /cm$^2$ in femoral neck were considered as osteoporotic.

In vertebrae, the mean change from baseline in osteopenic/osteoporotic subjects (BMD T score below −1) was 7.3% in 2 mg of $E_2V$ group, 7.7% in 1 mg $E_2V$ and 9.4% in 1 mg/$^2$ mg $E_2V$ group, no significant differences were seen. For the group with normal BMD, corresponding changes were 7.5%, 4.7% and 8.3%. Both the 1 mg/$^2$ mg $E_2V$ group and 2 mg of $E_2V$ group differed statistically significantly from the 1 mg E2V group $p<0.001$).

Vertebral BMD and change (%) in BMD from baseline can be seen in FIG. 1.

In femoral neck, the BMD changes ranged from 2.1% to 2.5% in the group that had normal BMD values at baseline. For osteopenic/osteoporotic subjects, the percentage changes were 6.4% for the 1 mg/2 mg $E_2V$ group, 3.5% for 2 mg $E_2V$ group and 3.8% for 1 mg of $E_2V$ group. The differences between 1 mg/2 mg of $E_2V$ group and the two other groups were statistically significant (1 mg/2 mg vs. 2 mg $p=0.0258$ and 1 mg /2 mg vs. 1 mg $p=0.0086$).

Figure 2:
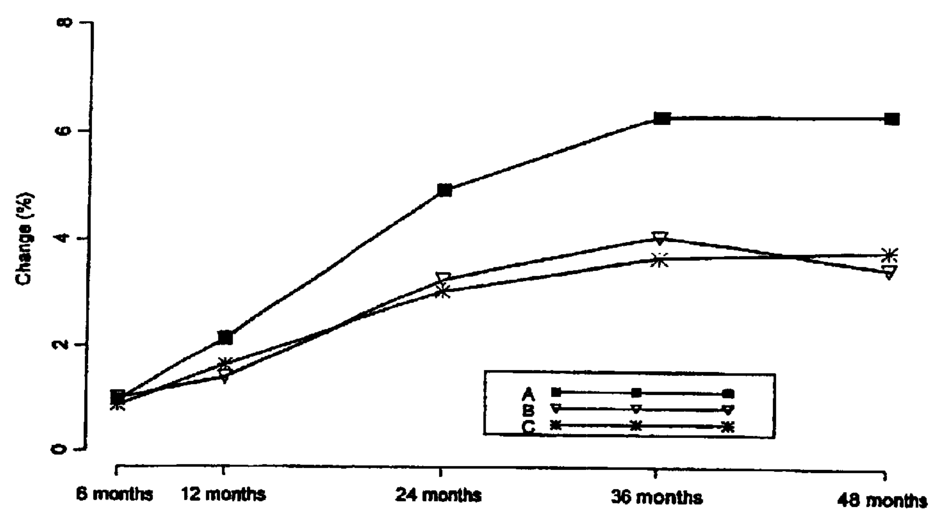
FIG. 2 shows the change (%) in bone mineral density in osteopenic and osteoprotic women in femoral neck.

Femoral BMD and change (%) in BMD from baseline can be seen in FIG. 2.

The most prominent increase for all incides measured was seen in women who had first been taken 1 mg $E_2V$ for 6 months before switching over to the 2 mg regimen. The baseline bone mineral density values were somewhat, but not significantly, lower in this group, which may explain the obvious superiority of this group in gaining bone mineral density after six months. However, there were no differences in baseline bone mineral density of women with low bone mass between the groups, and nevertheless greater vertebral and particularly femoral bone mineral density increases were seen in these women. Furthermore, about half of women in each group had used some kind of HRT previously. Thus, there was no unbalanced distribution of previous HRT users in the three groups which could have been resulted in slower bone mineral density gain in group with a higher number of previous users. Morever, there were no other differences in the baseline characteristics between the groups that could have affected the results.

Although the invention has been illustrated by the preceding example, it is not to be construed as being limited to the materials employed therein; rather, the invention is directed to the genetric area as herein disclosed. Various modifications and embodiments thereof can be made without departing from the spirit or scope thereof

What is claimed is:

1. A method for the prevention or treatment of postmenopausal osteoporosis, which comprises initiating the prevention or treatment with a low dose of an estrogenic compound for about 4 to about 8 months and after this initiation period increasing the amount of the estrogenic compound.

2. The method according to claim 1, wherein the initiation period lasts about 8 months.

3. The method according to claim 1, wherein the amount of the estrogenic compound is doubled after the initiation period.

4. The method according to claim 1, wherein the close of the estrogenic compound in the initiation period is a dose equivalent in estrogenic activity to approximately 0.5 to approximately 1.5 mg of estraliol valerate.

5. The method according to claim 4, wherein the dose of the estrogenic compound in the initiation period is a dose equivalent in estrogenic activity to approximately 1 mg of estradiol valerate.

6. The method according to claim 1, wherein the initiation period lasts from about 4 to about 6 months.

7. The method according to claim 1, wherein the initiation period lasts from about 6 to about 8 months.

8. The method according to claim 1, wherein the estrogenic compound is estradiol valerate.

9. The method according to claim 1, wherein the estrogenic compound is estrone, estrone sulphate, an estrone sulphate piperazine salt or an ester thereof, or a synthetic estrogen.

10. A method according to claim 1, wherein the amount of the estrogenic compound is increased by about 33% to about 100% after the initiation period.

11. A method for the prevention or treatment of postmenopausal osteoporosis, which comprises initiating the prevention or treatment with a low dose of an estrogenic compound and after this initiation period increasing the amount of the estrogenic compound and maintaining the increased amount for at least about 6 months.

12. A method for the prevention or treatment of postmenopausal osteoporosis, which comprises initiating the prevention or treatment with a daily dose of approximately 1 mg of estradiol valerate for an initiation period of about 8 months and then increasing the daily dose of estraciol valerate to approximately 2 mg after initiation period.

* * * * *

UNITED STATES PATENT AND TRADEMARK OFFICE
CERTIFICATE OF CORRECTION

PATENT NO. : 6,846,496 B1
DATED : January 25, 2005
INVENTOR(S) : Ulla Timonen and Raija Vaheri It is certified that error appears in the above-identified patent and that said Letters Patent is hereby corrected as shown below:

Title page,
Item [57], ABSTRACT,
Line 2, "close" should read -- dose --.

Column 4,
Line 67, "8" should read -- 6 --.

Column 5,
Line 4, "close" should read -- dose --.
Line 7, "estraliol" should read -- estradiol --.
Line 18, "salt or" should read -- salt, or --.

Column 6,
Line 14, "8" should read -- 6 --.
Line 15, "estraciol" should read -- estradiol --.
Line 16, "after initiation" should read -- after the initiation --.

Signed and Sealed this

Third Day of May, 2005

JON W. DUDAS
*Director of the United States Patent and Trademark Office*